United States Patent
Higuchi et al.

(10) Patent No.: US 9,541,523 B2
(45) Date of Patent: Jan. 10, 2017

(54) SENSOR CONTROL APPARATUS AND GAS DETECTION SYSTEM

(71) Applicant: NGK SPARK PLUG CO., LTD., Nagoya-shi, Aichi (JP)

(72) Inventors: Yuzo Higuchi, Komaki (JP); Tomonori Uemura, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 386 days.

(21) Appl. No.: 14/224,349

(22) Filed: Mar. 25, 2014

(65) Prior Publication Data

US 2014/0290337 A1 Oct. 2, 2014

(30) Foreign Application Priority Data

Mar. 27, 2013 (JP) ................................. 2013-066736

(51) Int. Cl.
*G01N 27/417* (2006.01)
(52) U.S. Cl.
CPC ................................. *G01N 27/417* (2013.01)
(58) Field of Classification Search
None
See application file for complete search history.

(56) References Cited

U.S. PATENT DOCUMENTS

| | | | |
|---|---|---|---|
| 4,767,520 A * | 8/1988 | Asakura et al. | 204/406 |
| 6,347,544 B1 | 2/2002 | Hada et al. | |
| 6,453,724 B1 | 9/2002 | Kawase et al. | |
| 6,868,712 B2 | 3/2005 | Hada et al. | |
| 7,043,957 B2 | 5/2006 | Hattori | |
| 8,345,397 B2 | 1/2013 | Ieda | |
| 2002/0056310 A1 | 5/2002 | Hada et al. | |
| 2004/0099041 A1 | 5/2004 | Hattori | |
| 2011/0199709 A1 | 8/2011 | Ieda | |

FOREIGN PATENT DOCUMENTS

| | | |
|---|---|---|
| JP | 11-6813 A | 1/1999 |
| JP | 2000-171439 A | 6/2000 |
| JP | 2004-177178 A | 6/2004 |
| JP | 2006-113081 A | 4/2006 |

(Continued)

OTHER PUBLICATIONS

Communication dated Apr. 26, 2016 issued by the Japanese Patent Office in counterpart application No. 2013-066736.

(Continued)

*Primary Examiner* — Robert R Raevis
(74) *Attorney, Agent, or Firm* — Sughrue Mion, PLLC

(57) ABSTRACT

A sensor control apparatus (2) of a gas detection system (1) includes a first low-pass filter (46), a second low-pass filter (48), and a multiplexer (50) so as to provide different time constants for detection of a sensor output signal Vs1 and for detection of a response signal Vs2. When the sensor output signal Vs1 is detected, a signal whose frequency band is the same as that of Vs1 is input to the analog-to-digital conversion section (31) through the first low-pass filter (46). Therefore, the detection accuracy of Vs1 is increased. When Vs2 is detected, a signal whose frequency band is the same as that of Vs2 is input to the analog-to-digital conversion section (31) through the second low-pass filter (48).

6 Claims, 7 Drawing Sheets

(56) References Cited

FOREIGN PATENT DOCUMENTS

| | | |
|---|---|---|
| JP | 2007-057544 A | 3/2007 |
| JP | 2008-008667 A | 1/2008 |
| JP | 2011-043523 A | 3/2011 |
| JP | 2011-520112 A | 7/2011 |
| JP | 2011-164035 A | 8/2011 |
| WO | 2009/135862 A1 | 11/2009 |

OTHER PUBLICATIONS

Communication dated Aug. 9, 2016 from the Japanese Patent Office in counterpart Application No. 2013-066736.

* cited by examiner

SENSOR CONTROL APPARATUS AND GAS DETECTION SYSTEM

BACKGROUND OF THE INVENTION

1. Field of the Invention

The present invention relates to a sensor control apparatus which controls a gas sensor including a sensor element whose sensor output signal changes in accordance with the concentration of a gas, and a gas detection system which includes the gas sensor and the sensor control apparatus.

2. Description of the Related Art

Conventionally, a gas detection system has been known including a sensor control apparatus which controls a gas sensor. The gas sensor has a sensor element which includes a first cell whose sensor output signal changes in accordance with the concentration of a gas.

As an example, the first cell is composed of a solid electrolyte body and a pair of electrodes, generates an electromotive force corresponding to the concentration of a specific gas (e.g., oxygen) contained in a gas under measurement (hereinafter also referred to as an "object gas"), and outputs a sensor output signal corresponding thereto.

Examples of a gas sensor including such a first cell are a linear lambda sensor which detects the concentration of oxygen contained in the object gas and an NO sensor which detects the concentration of NO contained in the object gas.

The sensor control apparatus controls operation of the sensor element such that a sensor output signal can be output therefrom, and reads the sensor output signal of the sensor element, to thereby detect the concentration of the specific gas on the basis of the sensor output signal.

Such a sensor element (first cell) may have the property of an impedance which changes with a change in its temperature (element temperature).

A sensor control apparatus which controls a gas sensor including such a sensor element operates as follows. The sensor control apparatus first supplies to the sensor element (the first cell) an impedance detection signal for detecting the impedance of the first cell, and reads a response signal output in response to the impedance detection signal. The sensor control apparatus can detect the impedance of the first cell on the basis of the read response signal, thereby detecting the element temperature of the sensor element.

As is generally known, a filter circuit having a frequency band suitable for a signal to be detected is provided in such a sensor control apparatus so as to remove high-frequency noise, to thereby ensure accurate detection of the signal.

[Patent Document 1] Japanese Patent Application Laid-Open (kokai) No. 2008-008667

3. Problems to be Solved by the Invention

However, in a sensor control apparatus configured so as to read a sensor output signal or a response signal output from the above-mentioned first cell, the detection accuracy of either one of these signals may be compromised.

Namely, since the frequency band of the sensor output signal and the response signal differ from each other, use of a filter circuit suitable for the frequency band of the sensor output signal may attenuate the response signal, thereby decreasing the detection accuracy of the response signal. In contrast, use of a filter circuit suitable for the frequency band of the response signal may superimpose noise on the sensor output signal, thereby decreasing the detection accuracy of the sensor output signal.

SUMMARY OF THE INVENTION

It is therefore an object of the present invention to provide a sensor control apparatus which is configured to read a sensor output signal and a response signal for use therein and which can suppress a decrease in the detection accuracy of these signals. Another object of the present invention is to provide a gas detection system which includes such a sensor control apparatus.

The above objects have been achieved, in accordance with a first aspect of the invention by providing (1) a sensor control apparatus for controlling a gas sensor including a sensor element which outputs a sensor output signal, the sensor output signal changing a change in with the concentration of a gas and which includes a first cell composed of a solid electrolyte body and a pair of electrodes. The sensor control apparatus comprises a detection signal generation section which generates an impedance detection signal for detecting the impedance of the first cell; an analog-to-digital conversion section which receives the sensor output signal, the sensor output signal changing with a change in the concentration of the gas, or which receives a response signal generated by the first cell in response to the impedance detection signal, and which converts the analog value of the sensor output signal or the response signal to a digital value, the sensor output signal and the response signal being output from the first cell; and a time-constant variable filter section which is a low-pass filter provided in a signal path between the first cell and the analog-to-digital conversion section and having a variable time constant. The time-constant variable filter section has a time constant which changes such that the time constant at the time when the sensor output signal is input to the analog-to-digital conversion section is greater than the time constant at the time when the response signal is input to the analog-to-digital conversion section.

As described above, a time-constant variable filter section is provided as a low-pass filter, and the time constant of the time-constant variable filter section is changed such that the time constant at the time when the sensor output signal is input to the analog-to-digital conversion section differs from the time constant at the time when the response signal is input to the analog-to-digital conversion section. Therefore, unlike the configuration in which the time constant is always fixed, the time constant can be changed in accordance with the type of input signal.

As compared with the response signal whose instantaneous change is large, the sensor output signal whose instantaneous change is small can be detected more accurately by using a low-pass filter having a large time constant. In contrast, as compared with the sensor output signal whose instantaneous change is small, the response signal whose instantaneous change is large can be detected more accurately by using a low-pass filter having a small time constant.

Therefore, by providing a time-constant variable filter section having a time constant which changes such that the time constant at the time when the sensor output signal is input to the analog-to-digital conversion section is greater than the time constant at the time when the response signal is input to the analog-to-digital conversion section, the detection accuracy of the sensor output signal and that of the response signal can be improved.

In other words, by changing the time constant of the time-constant variable filter section to thereby change the frequency band of signals that pass through the time-constant variable filter section, the frequency band of the time-constant variable filter section can be changed in accordance the frequency band of the sensor output signal or the response signal. Namely, when the sensor output signal is input, the frequency band of the time-constant variable filter section is changed to include the frequency band of the sensor output signal, and when the response signal is input, the frequency band of the time-constant variable filter section is changed to include the frequency band of the response signal. Thus, the detection accuracy of each signal can be increased.

Accordingly, the present invention can suppress a decrease in the detection accuracy of the sensor output signal and the response signal in a sensor control apparatus which is configured to read these signals for use therein.

In a preferred embodiment (2) of the sensor control apparatus (1), the gas sensor includes a heater which brings the first cell into an activated state by supplying an energization current to the heater, and the impedance detection signal is generated by the detection signal generation section after a predetermined wait time has elapsed after a time at which the energization current has been switched on.

Immediately after the energization current supplied to the heater is switched on, noise is generated as a result of the energization current switching. However, since the noise has a decreased level after the wait time has elapsed, the influence of the noise on detection of the response signal can be mitigated.

Therefore, the present invention can suppress a decrease in the detection accuracy of the response signal.

In another preferred embodiment (3) of the sensor control apparatus of (1) or (2) above, the time-constant variable filter section includes a first low-pass filter which is used when the sensor output signal is input to the analog-to-digital conversion section; a second low-pass filter which has a time constant smaller than that of the first low-pass filter and which is used when the response signal is input to the analog-to-digital conversion section; and a filter switching section which connects the first low-pass filter between the first cell and the analog-to-digital conversion section when the sensor output signal is input to the analog-to-digital conversion section and which connects the second low-pass filter between the first cell and the analog-to-digital conversion section when the response signal is input to the analog-to-digital conversion section.

Namely, in this time-constant variable filter section, the filter switching section selects one of the first and second low-pass filters as a low-pass filter to be connected between the first cell and the analog-to-digital conversion section.

By virtue of this configuration, the sensor control apparatus can render the time constant of the time-constant variable filter section at the time of input of the sensor output signal greater than the time constant of the time-constant variable filter section at the time of input of the response signal, whereby the detection accuracy of the sensor output signal and that of the response signal can be improved.

In yet another preferred embodiment (4) of the sensor control apparatus of (1) or (2) above, the time-constant variable filter section includes a single capacitor element; a plurality of resistor elements; and a connection state changeover section which forms a low-pass filter composed of the capacitor element and at least one of the resistor elements by connecting the capacitor element and the at least one resistor element, the connection state changeover section changing the time constant of the low-pass filter by changing the state of connection between the capacitor element and the at least one resistor element.

Namely, in this time-constant variable filter section, the connection state changeover section changes the time constant of the low-pass filter composed of the capacitor element and the at least one resistor element by changing the state of connection between the capacitor element and the at least one resistor element.

By virtue of this configuration, the sensor control apparatus can render the time constant of the time-constant variable filter section at the time of input of the sensor output signal greater than the time constant of the time-constant variable filter section at the time of input of the response signal, whereby the detection accuracy of the sensor output signal and that of the response signal can be improved.

In yet another preferred embodiment (5) of the sensor control apparatus of any of (1) to (4) above, the sensor element further includes a second cell composed of a solid electrolyte body and a pair of electrodes; and the sensor control apparatus comprises a digital computation section which computes, through digital computation, a control signal for controlling energization of the second cell, on the basis of the sensor output signal whose analog value is converted to a digital value by the analog-to-digital conversion section.

In this case, the sensor control apparatus can accurately compute the control signal for controlling the energization of the second cell at the digital computation section.

In a second aspect (6), the present invention provides a gas detection system comprising a gas sensor including a sensor element which outputs a sensor output signal changing with the concentration of a gas and which includes a first cell composed of a solid electrolyte body and a pair of electrodes; and the sensor control apparatus for controlling the gas sensor as described in any of (1) to (5) above.

Since this gas detection system includes any one of the above-described sensor control apparatuses, like the above-described sensor control apparatuses, the gas detection system can improve the detection accuracy of the sensor output signal and that of the response signal. This is because signals having frequency bands corresponding to those of the sensor output signal and the response signal are selectively input to the analog-to-digital conversion section.

Therefore, the gas detection system of the present invention can prevent a decrease in the detection accuracy of the sensor output signal and that of the response signal, even in the case where the gas detection apparatus is configured to read these signals for use therein.

DESCRIPTION OF REFERENCE NUMERALS

Figure 1:
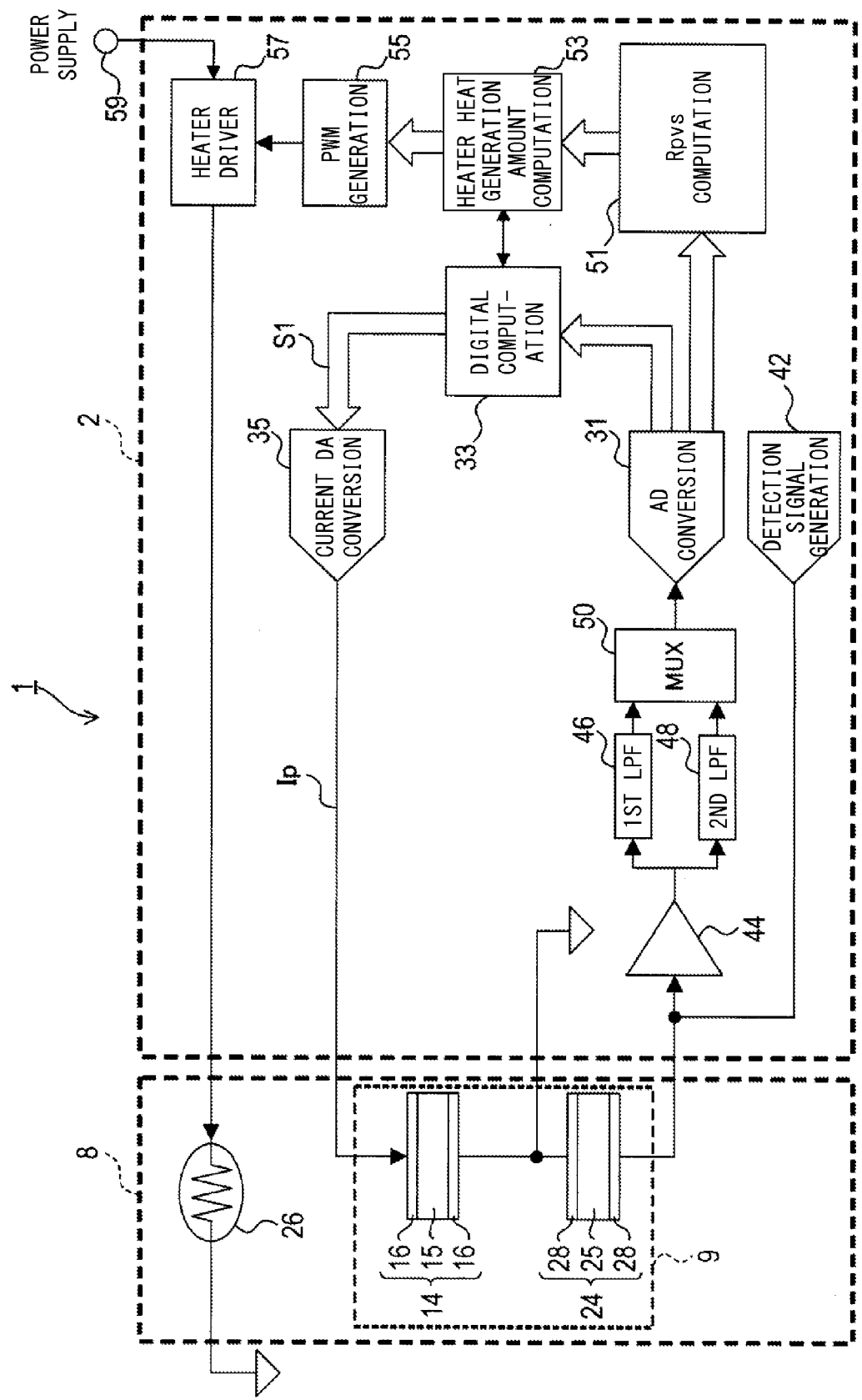
FIG. 1 is a block diagram showing the overall configuration of a gas detection system.

Reference numerals used to identify various features in the drawings including the following.

1: gas detection system
2: sensor control apparatus

8: gas sensor
9: sensor element
14: pump cell
24: electromotive force cell
26: heater
31: AD conversion section (analog-to-digital conversion section)
33: digital computation section
35: current DA conversion section (current digital-to-analog conversion section)
42: detection signal generation section
46: first low-pass filter
48: second low-pass filter
50: multiplexer
51: Rpvs computation section
53: heater heat generation amount computation section
55: PWM generation section
57: heater driver
59: power supply apparatus
61: first resistor element
63: first capacitor
65: second resistor element
67: second capacitor
71: first switch
73: second switch
81: variable low-pass filter
83: third resistor element
84: third switch
85: fourth resistor element
86: fourth switch
87: second capacitor element
91: second variable low-pass filter
93: fifth resistor element
94: sixth resistor element
95: fifth switch
96: third capacitor element
101: second gas detection system
102: second sensor control apparatus

DETAILED DESCRIPTION OF THE PREFERRED EMBODIMENTS

Embodiments of the present invention will now be described with reference to FIGS. 1 to 8. However, the present invention should not be construed as being limited thereto or to the embodiments which will be described below, and may be implemented in various forms without departing from the spirit and scope of the claims appended hereto.

1. First Embodiment

[1-1. Overall Configuration]
FIG. 1 is a block diagram showing the overall configuration of a gas detection system 1 which is an embodiment of the present invention.

The gas detection system 1 is used to detect, for example, a specific gas (oxygen in the present embodiment) contained in exhaust gas which is discharged from an internal combustion engine.

The gas detection system 1 includes a gas sensor 8 which detects oxygen and a sensor control apparatus 2 which controls the gas sensor 8. The gas detection system 1 notifies an engine control apparatus (unillustrated) of the detected oxygen concentration.

The engine control apparatus is a microcontroller which performs various kinds of control processing in order to control the internal combustion engine. For example, the engine control apparatus controls the air-fuel ratio of the internal combustion engine by use of the oxygen concentration detected by the gas detection system 1.

The gas sensor 8 is disposed in an exhaust pipe of the internal combustion engine so as to detect the oxygen concentration of the exhaust gas over a wide range, and is also referred to as a linear lambda sensor. The gas sensor 8 is composed of a sensor element 9 and a heater 26.

The sensor element 9 is composed of a pump cell 14 and an electromotive force cell 24.

The pump cell 14 is composed of an oxygen-ion-conducting solid electrolyte body 15 which is formed of partially-stabilized zirconia ($ZrO_2$), and a pair of porous electrodes 16 which are mainly formed of platinum and which are provided on the front and back surfaces of the solid electrolyte body 15. The electromotive force cell 24 is composed of an oxygen-ion-conducting solid electrolyte body 25 which is formed of partially-stabilized zirconia ($ZrO_2$), and a pair of porous electrodes 28 which are mainly formed of platinum and which are provided on the front and back surfaces of the solid electrolyte body 25.

The heater 26 is composed of a heating resistor which produces heat when externally energized. The heater 26 is provided in order to heat the pump cell 14 and the electromotive force cell 24, thereby bringing them into an activated state.

Notably, the gas sensor 8 includes a measurement chamber (unillustrated) between the pump cell 14 and the electromotive force cell 24 that is located inside the gas sensor 8 with a porous diffusion layer (unillustrated) intervening between the measurement chamber and the atmosphere. An object gas (exhaust gas in the present embodiment) is introduced into the measurement chamber through the porous diffusion layer.

By use of the electromotive force cell 24, the gas sensor 8 generates an electromotive force (detection voltage Vs) corresponding to the oxygen concentration in the measurement chamber (in other words, the oxygen concentration of the object gas introduced into the measurement chamber through the porous diffusion layer). Specifically, the electromotive force cell 24 generates a detection voltage Vs corresponding to the difference in oxygen concentration between the front and back porous electrodes 28 of the electromotive force cell 24. Namely, the detection voltage Vs output from the electromotive force cell 24 changes with the oxygen concentration in the measurement chamber.

In addition, by use of the pump cell 14, the gas sensor 8 pumps out oxygen contained in the object gas within the measurement chamber and pumps oxygen into the measurement chamber such that the detection voltage Vs from the electromotive force cell 24 becomes equal to a predetermined reference value (e.g., approx. 450 mV). Specifically, the gas sensor 8 causes a pump current Ip to flow between the front and back porous electrodes 16 of the pump cell 14 in order to pump oxygen out of and into the measurement chamber, thereby adjusting the oxygen concentration in the measurement chamber.

Namely, the gas sensor 8 is used to detect the oxygen concentration of the object gas on the basis of the pump current Ip applied to the pump cell 14 such that the oxygen concentration in the measurement chamber becomes equal to a predetermined target concentration (e.g., a concentration corresponding to the stoichiometric air-fuel ratio).

The sensor control apparatus 2 detects the oxygen concentration of the exhaust gas by driving and controlling the gas sensor 8, and notifies the engine control apparatus (unillustrated) of the detected oxygen concentration.

The sensor control apparatus 2 includes an AD conversion section 31 (analog-to-digital conversion section 31), a digital computation section 33, a current DA conversion section 35 (current digital-to-analog conversion section 35), a detection signal generation section 42, a buffer 44, a first low-pass filter 46 (first LPF 46), a second low-pass filter 48 (second LPF 48), a multiplexer 50, an Rpvs computation section 51, a heater heat generation amount computation section 53, a PWM generation section 55, and a heater driver 57.

The detection signal generation section 42 inputs an impedance detection signal Sa to the electromotive force cell 24 of the gas sensor 8 in order to detect the internal resistance of the electromotive force cell 24 of the gas sensor 8. Specifically, the detection signal generation section 42 applies a constant current (i.e., an impedance detection signal Sa) to the electromotive force cell 24 in response to an instruction from the digital computation section 33.

The buffer 44 detects the voltage generated across the electromotive force cell 24 (the voltage generated between the opposite terminals (ends) of the electromotive force cell 24; hereinafter also referred to as the "inter-terminal voltage of the electromotive force cell 24") at high impedance, and outputs it to the first low-pass filter 46 or the second low-pass filter 48 at low impedance. Notably, when the impedance detection signal Sa is not input, the inter-terminal voltage of the electromotive force cell 24 becomes a sensor output signal Vs1 (detection voltage Vs) which changes with the oxygen concentration in the measurement chamber. In contrast, when the impedance detection signal Sa is input, the inter-terminal voltage of the electromotive force cell 24 becomes a response signal Vs2 which changes with the internal resistance of the electromotive force cell 24.

The first low-pass filter 46 is a filter whose time constant is set in accordance with the sensor output signal Vs1 which changes with a change in the oxygen concentration in the measurement chamber. Of the signals received from the buffer 44, the first low-pass filter 46 allows only signals (including the sensor output signal Vs1) within a predetermined frequency band to pass therethrough.

Namely, the first low-pass filter 46 is a filter which extracts the sensor output signal Vs1 which changes with a change in the oxygen concentration in the measurement chamber from those signals which change with a change in the inter-terminal voltage of the electromotive force cell 24, and outputs the extracted sensor output signal Vs1.

The second low-pass filter 48 is a filter which allows signals to pass therethrough within the same frequency band as that of the response signal Vs2 which changes with a change in the internal resistance of the electromotive force cell 24. Namely, the second low-pass filter 48 extracts the response signal Vs2 which changes with the internal resistance of the electromotive force cell 24 from the signal which changes with the inter-terminal voltage of the electromotive force cell 24, and outputs the extracted response signal Vs2.

That is, among signals which change with the inter-terminal voltage generated between opposite ends (terminals) of the electromotive force cell 24, the sensor output signal Vs1 which changes with a change in the oxygen concentration in the measurement chamber passes through the first low-pass filter 46. Meanwhile, among those signals which change with the inter-terminal voltage generated between the opposite ends of the electromotive force cell 24, the response signal Vs2 which changes with a change in the internal resistance of the electromotive force cell 24 passes through the second low-pass filter 48.

Figure 2:
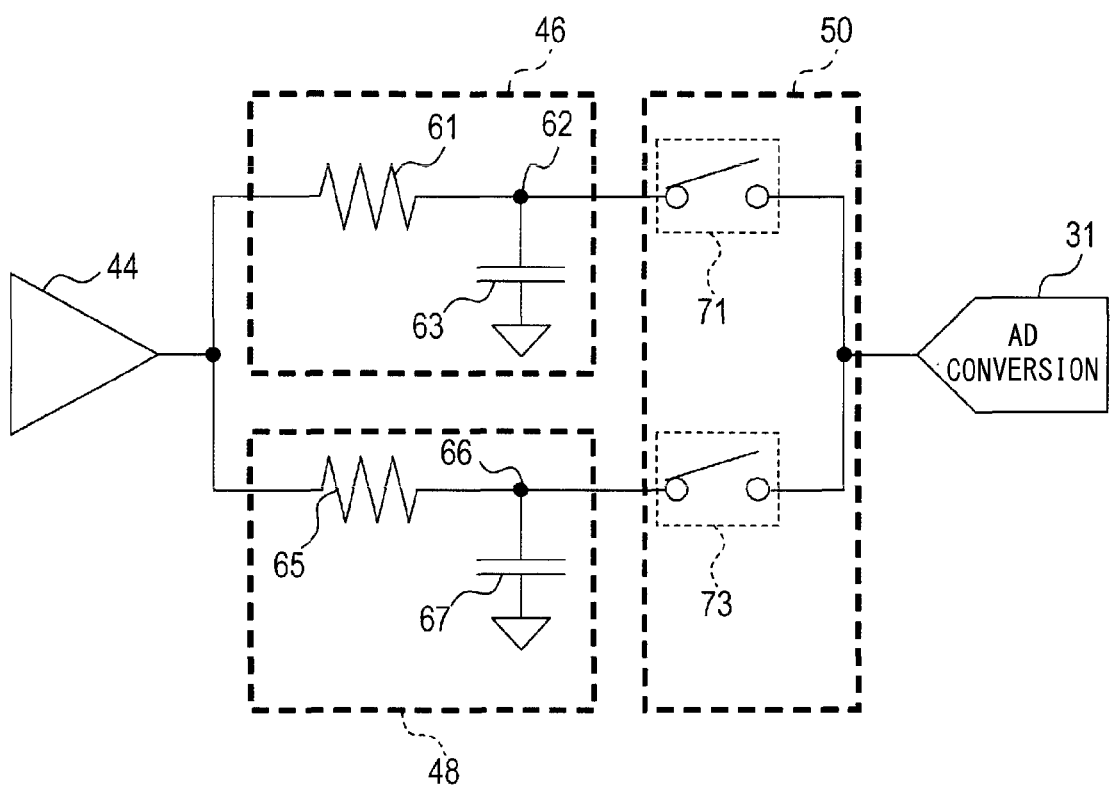
FIG. 2 is an explanatory diagram showing the internal configurations of a first low-pass filter, a second low-pass filter, and a multiplexer.

FIG. 2 is an explanatory diagram showing the internal configurations of the first low-pass filter 46, the second low-pass filter 48 and the multiplexer 50.

The first low-pass filter 46, the second low-pass filter 48, and the multiplexer 50 are provided in a common line between the electromotive force cell 24 and the AD conversion section 31.

The first low-pass filter 46 is a filter circuit which includes a first resistor element 61 and a first capacitor 63. The first resistor element 61 having a resistance of 50 kΩ is connected between the buffer 44 and the multiplexer 50 (specifically, a first switch 71). The first capacitor 63 having a capacitance of 22 nF is connected between the ground line and a connection point 62 at which the first resistor element 61 and the multiplexer 50 are connected together.

The time constant T1 of the first low-pass filter 46 is 1100 μsec (=50 kΩ×22 nF), and the cutoff frequency f1 of the first low-pass filter 46 is 0.14 kHz (=$1/(2\pi\tau 1)$).

The second low-pass filter 48 is a filter circuit which includes a second resistor element 65 and a second capacitor 67. The second resistor element 65 having a resistance of 0.270 kΩ is connected between the buffer 44 and the multiplexer 50 (specifically, a second switch 73). The second capacitor 67 having a capacitance of 22 nF is connected between the ground line and a connection point 66 at which the second resistor element 65 and the multiplexer 50 are connected together.

The time constant $\tau 2$ of the second low-pass filter 48 is 5.94 μsec (=0.270 kΩ×22 nF), and the cutoff frequency f2 of the second low-pass filter 48 is 26.8 kHz (=$1/(2\pi\tau 2)$).

That is, the time constant $\tau 1$ of the first low-pass filter 46 is greater than the time constant $\tau 2$ of the second low-pass filter 48. In addition, the cutoff frequency f1 of the first low-pass filter 46 is lower than the cutoff frequency f2 of the second low-pass filter 48.

The multiplexer 50 (hereinafter also referred to as the MUX 50) outputs to the AD conversion section 31 either one of the signal received from the first low-pass filter 46 and the signal received from the second low-pass filter 48. The multiplexer 50 determines which one of these signals is to be output on the basis of an instruction from the digital computation section 33.

The multiplexer 50 includes the first switch 71 and the second switch 73. The first switch 71 is connected between the first low-pass filter 46 and the AD conversion section 31, and the second switch 73 is connected between the second low-pass filter 48 and the AD conversion section 31.

The sates (ON state and OFF state) of the first switch 71 and the second switch 73 are set based on an instruction from the digital computation section 33. Specifically, when the sensor output signal Vs1 is detected, the first switch 71 is set to the ON state and the second switch 73 is set to the OFF state. When the response signal Vs2 is detected, the first switch 71 is set to the OFF state and the second switch 73 is set to the ON state.

Returning back to FIG. 1, the AD conversion section 31 converts to a digital value the analog value of the inter-terminal voltage (generated across the electromotive force cell 24 of the gas sensor 8) which is received through the first low-pass filter 46 or the second low-pass filter 48, and notifies the digital computation section 33 or the Rpvs computation section 51 of the digital value of the inter-terminal voltage. Specifically, the AD conversion section 31 notifies the digital computation section 33 of the digital value of the sensor output signal Vs1, and notifies the Rpvs computation section 51 of the digital values of the response signal Vs2 and the sensor output signal Vs1.

The digital computation section 33 performs computation control processing, such as sensor control processing and pump current control processing, and switching of the states (ON state and OFF state) of the first switch 71 and the second switch 73. The sensor control processing will be described below.

Notably, the sensor control apparatus 2 includes an unillustrated EEPROM and an unillustrated RAM.

The EEPROM is a storage section which stores programs for the computation control processing, various parameters used for computation control processing, and other processing parameters. In addition, the EEPROM stores various pieces of information (maximum allowable current of the pump cell 14, etc.) which are determined in accordance with the type and characteristics of the gas sensor 8 (i.e., a target for control). These pieces of information are stored in the EEPROM during the fabrication of the sensor control apparatus 2.

The RAM is a storage section which temporarily stores control data used for various kinds of computation control processing, and other tasks.

The pump current control processing is computation control processing which controls the pump current Ip to be supplied to the pump cell 14 such that the detection voltage Vs from the electromotive force cell 24 becomes equal to a target control voltage (e.g., 450 mV in the present embodiment).

Specifically, the digital computation section 33, which performs the pump current control processing, performs PID computation based on a deviation ΔVs between the target control voltage (450 mV) and the detection voltage Vs from the electromotive force cell 24, and controls, by use of the current DA conversion section 35, the pump current Ip to be supplied to the pump cell 14 such that the deviation ΔVs approaches 0 (in other words, such that the detection voltage Vs approaches the target control voltage).

The digital computation section 33 sends to the current DA conversion section 35 a DAC control signal 51 which represents information relating to the pump current Ip. The DAC control signal 51 is a digital signal which represents information relating to the magnitude and flow direction (forward direction or reverse direction) of the pump current Ip.

The current DA conversion section 35 performs DA conversion based on the DAC control signal 51 received from the digital computation section 33 and representing the information relating to the pump current Ip, and applies the pump current Ip to the pump cell 14.

The current DA conversion section 35 receives from the digital computation section 33 the DAC control signal 51 representing the information (flow direction and magnitude of current) relating to the pump current Ip, performs DA conversion in accordance with the received digital information, and applies to the pump cell 14 a pump current (i.e., the pump current Ip) determined based on the DAC control signal S1.

The Rpvs computation section 51 computes the internal resistance Rpvs of the electromotive force cell 24 based on the digital values of the response signal Vs2 and the sensor output signal Vs1 notified by the AD conversion section 31.

The heater heat generation amount computation section 53 obtains, through digital computation, the actual temperature of the gas sensor 8 based on the internal resistance Rpvs computed by the Rpvs computation section 51, and computes a heater heat generation amount which is necessary to make the actual temperature of the gas sensor 8 approach the sensor target temperature.

The PWM signal generation section 55 computes the duty ratio of the power supplied to the heater 26 based on the heater heat generation amount computed by the heater heat generation amount computation section 53, and generates a PWM control signal corresponding to the duty ratio.

By use of the power supplied from a power supply apparatus 59, the heater driver 57 energizes the heater 26, while controlling the energization based on the PWM control signal received from the PWM signal generation section 55. Thus, the heater can produce heat which is needed to make the actual temperature of the gas sensor 8 approach the sensor target temperature.

[1-2. Sensor Control Processing]

Next, the sensor control processing will be described which is performed by the digital computation section 33 of the sensor control apparatus 2.

Figure 3:
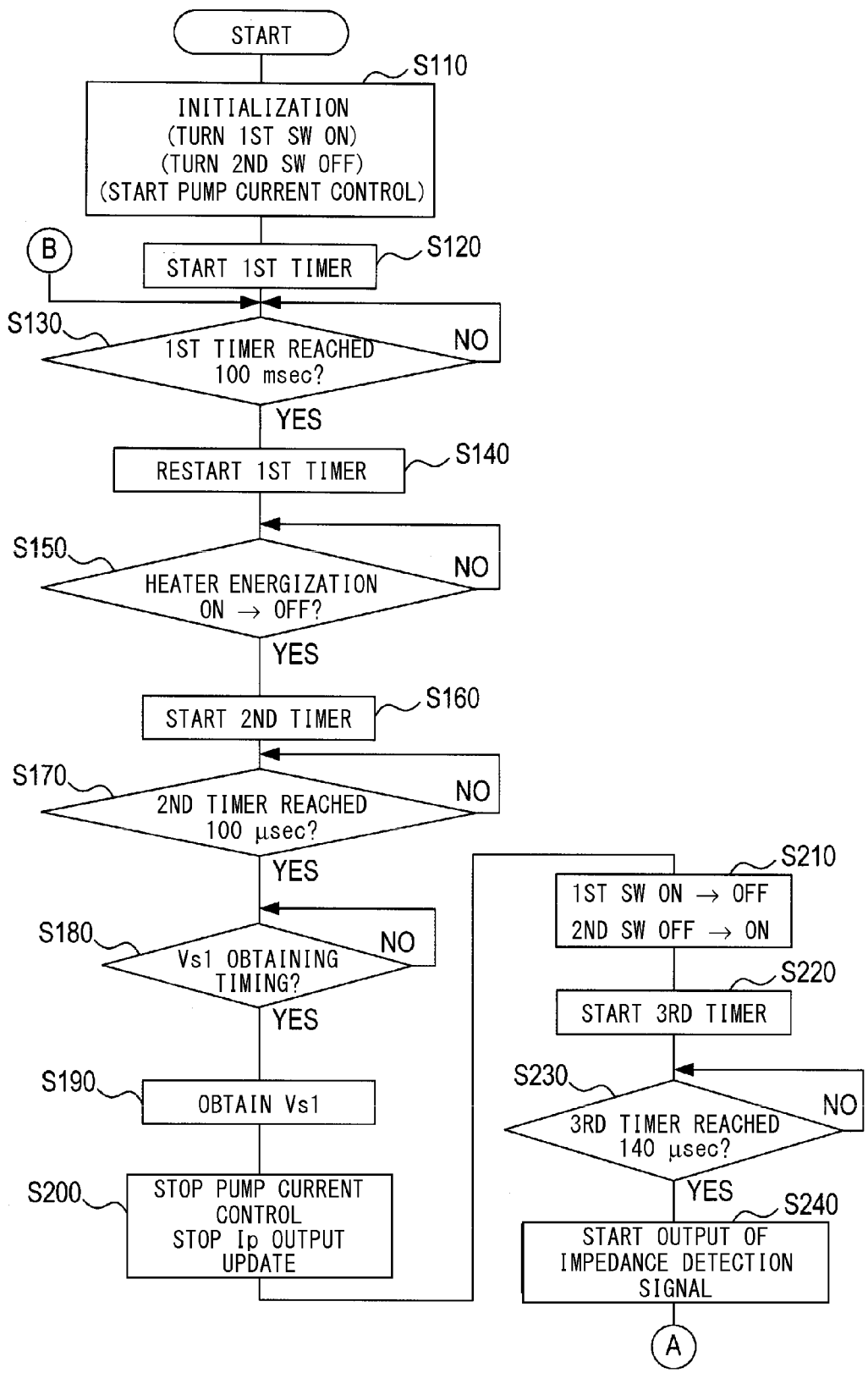
FIG. 3 is a flowchart showing a part of a sensor control processing routine.
Figure 4:
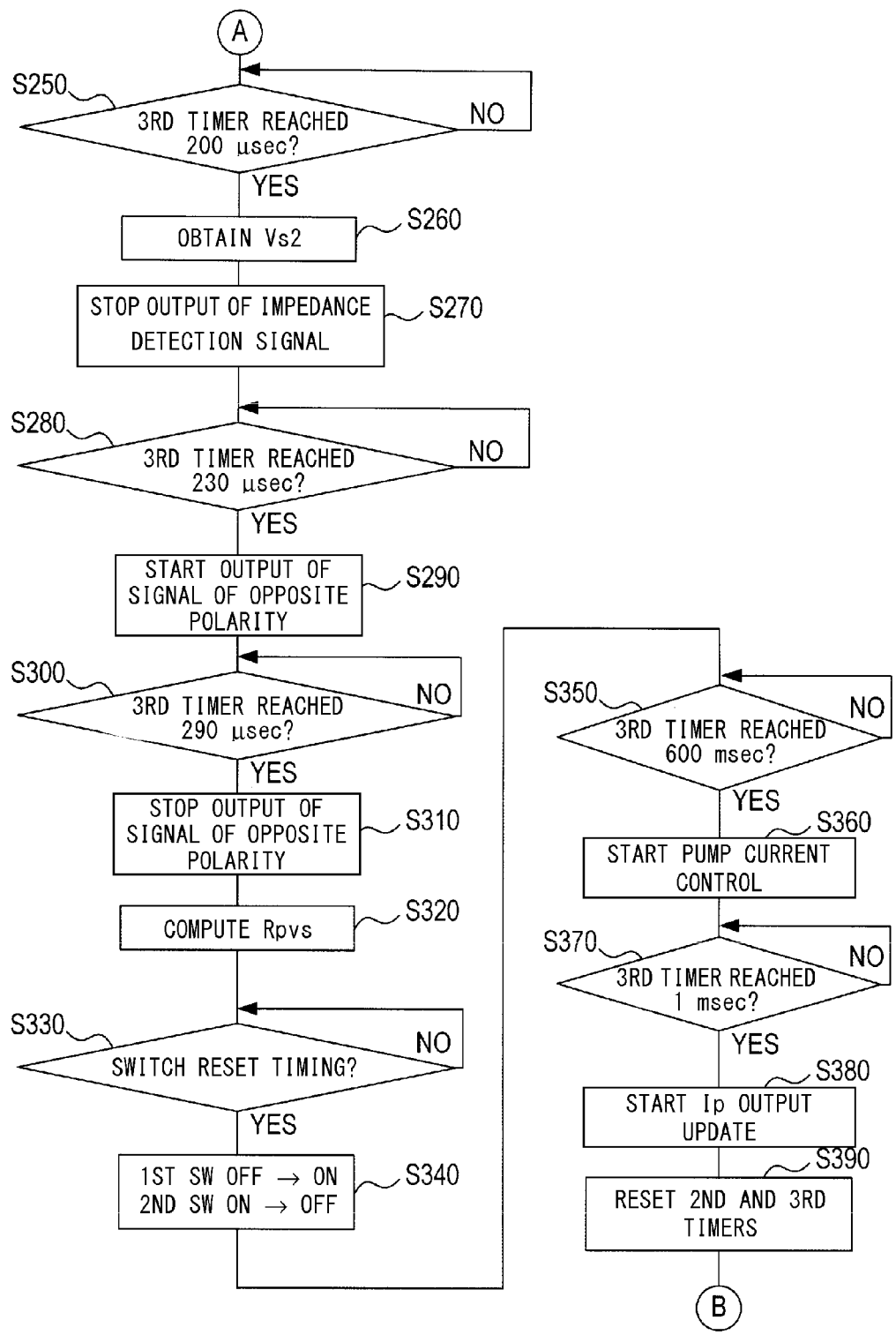
FIG. 4 is a flowchart showing the remaining part of the sensor control processing routine.

FIGS. 3 and 4 are flowcharts showing the details of the sensor control processing routine.

The sensor control processing routine starts when the sensor control apparatus 2 is started.

Upon start of the sensor control processing routine, in S110 (S represents "step"), the digital computation section 33 performs initialization. Specifically, the digital computation section 33 sets the first switch 71 to the ON state, sets the second switch 73 to the OFF state, and starts the pump current control processing.

As described above, the pump current control processing is computation control processing for controlling the pump current Ip to be supplied to the pump cell 14 such that the detection voltage Vs from the electromotive force cell 24 becomes equal to the target control voltage (e.g., 450 mV in the present embodiment). The pump current control processing and the sensor control processing are performed in parallel.

In S120 subsequent thereto, the digital computation section 33 starts a time measurement using a first timer.

In S130 subsequent thereto, the digital computation section 33 determines whether or not 100 msec has elapsed since start of the time measurement using the first timer. In the case where the digital computation section 33 makes a "Yes" determination, it proceeds to S140. In the case where the digital computation section 33 makes a "No" determination, it repeatedly executes S130, thereby waiting until 100 msec elapses.

Upon proceeding to S140 after making an "Yes" determination in S130, the digital computation section 33 restarts the time measurement using the first timer.

In S150 subsequent thereto, the digital computation section 33 determines whether or not the state of energization of the heater 26 has been changed from the ON state to the OFF state. In the case where the digital computation section 33 makes a "Yes" determination, it proceeds to step 160. In the case where the digital computation section 33 makes a "No" determination, it repeatedly executes S150 until the state of energization of the heater 26 is changed from the ON state to the OFF state.

Notably, energization of the heater 26 is controlled by the heater heat generation amount computation section 53, and in S150, the digital computation section 33 determines the state (ON state or OFF state) of energization of the heater 26 on the basis of the signal received from the heater heat generation amount computation section 53.

Upon proceeding to S160 after making a "Yes" determination in S150, the digital computation section 33 restarts time measurement using a second timer.

In S170 subsequent thereto, the digital computation section 33 determines whether or not 100 μsec has elapsed since start of the time measurement using the second timer. In the case where the digital computation section 33 makes a "Yes" determination, it proceeds to S180. In the case where the digital computation section 33 makes a "No" determination, it repeatedly executes S170, thereby waiting until 100 μsec elapses.

Notably, the wait time measured in S170 is set such that it is longer than a time required for the noise generated as a result of switching of the current supplied to the heater 26 to attenuate sufficiently.

Upon proceeding to S180 after making a "Yes" determination in S170, the digital computation section 33 determines whether or not the timing to obtain the sensor output signal Vs1 has come about. In the case where the digital computation section 33 makes a "Yes" determination, it proceeds to S190. In the case where it makes a "No" determination, it repeatedly executes S180, thereby waiting until the timing to obtain the sensor output signal Vs1 comes about.

In S180, the digital computation section 33 determines, as the timing to obtain the sensor output signal Vs1, the timing that comes first after making a "Yes" determination in step 170, among the timings at which the sampling period signal of the AD conversion section 31 changes from the high level to the low level.

Upon proceeding to S190 after making a "Yes" determination in S180, the digital computation section 33 obtains the sensor output signal Vs1. Notably, the sensor output signal Vs1 represents the inter-terminal voltage of the electromotive force cell 24 at the time before input of the impedance detection signal Sa. The sensor output signal Vs1 is used as the detection voltage Vs, and is also used in the processing of computing the internal resistance Rpvs of the electromotive force cell 24 (S320 described below).

In S200 subsequent thereto, the digital computation section 33 stops the pump current control processing and the Ip output update processing.

The Ip output update processing refers to the processing of outputting the oxygen concentration detected based on the pump current Ip to the engine control apparatus (unillustrated) via an unillustrated communication path. Thus, the sensor control apparatus 2 notifies the engine control apparatus (unillustrated) of the oxygen concentration detected by driving and controlling the gas sensor 8.

In S210 subsequent thereto, the digital computation section 33 switches the state of the first switch 71 from the ON state to the OFF state, and switches the state of the second switch 73 from the OFF state to the ON state.

In S220 subsequent thereto, the digital computation section 33 starts time measurement using a third timer.

In S230 subsequent thereto, the digital computation section 33 determines whether or not 140 μsec has elapsed since start of the time measurement using the third timer. In the case where the digital computation section 33 makes a "Yes" determination, it proceeds to S240. In the case where the digital computation section 33 makes a "No" determination, it repeatedly executes S230, thereby waiting until 140 μsec elapses.

Upon proceeding to S240 after making a "Yes" determination in S230, the digital computation section 33 instructs the detection signal generation section 42 to start outputting the impedance detection signal Sa. Thus, the detection signal generation section 42 inputs a −1.22 mA pulse signal to the electromotive force cell 24.

In S250 subsequent thereto, the digital computation section 33 determines whether or not 200 μsec has elapsed since start of the time measurement using the third timer.

In the case where the digital computation section 33 makes a "Yes" determination, it proceeds to step 260. In the case where the digital computation section 33 makes a "No" determination, it repeatedly executes S250, thereby waiting until 200 μsec elapses.

Upon proceeding to S260 after making a "Yes" determination in S250, the digital computation section 33 obtains the response signal Vs2. The response signal Vs2 obtained here is a signal which is generated by the electromotive force cell 24 in response to the impedance detection signal Sa supplied thereto, and its value corresponds to the current value (−1.22 mA) of the impedance detection signal Sa and the internal resistance Rpvs of the electromotive force cell 24.

In S270 subsequent thereto, the digital computation section 33 instructs the detection signal generation section 42 to stop the output of the impedance detection signal Sa. Thus, the detection signal generation section 42 stops the output of the pulse signal to the electromotive force cell 24.

In S280 subsequent thereto, the digital computation section 33 determines whether or not 230 μsec has elapsed since start of the time measurement using the third timer. In the case where the digital computation section 33 makes an "Yes" determination, it proceeds to S290. In the case where the digital computation section 33 makes a "No" determination, it repeatedly executes S280, thereby waiting until 230 μsec elapses.

Upon proceeding to S290 after making a "Yes" determination in S280, the digital computation section 33 instructs the detection signal generation section 42 to start outputting a reverse-polarity signal Sb. Thus, the detection signal generation section 42 inputs a +1.22 mA pulse signal to the electromotive force cell 24.

Notably, the reverse-polarity signal Sb refers to a pulse signal having a polarity opposite that of the impedance detection signal Sa. By supplying the reverse-polarity signal Sb to the electromotive force cell 24 as described above, there can be shortened the time needed for the electromotive force cell 24 to return to a normal state from an abnormal state can be shortened. The abnormal state is one where the electromotive force cell 24 fails to output a to-be-output internal electromotive force corresponding to the difference in the oxygen concentration due to the influence of the orientation of the solid electrolyte 25 constituting the electromotive force cell 24.

In S300 subsequent thereto, the digital computation section 33 determines whether or not 290 μsec has elapsed since start of the time measurement using the third timer. In the case where the digital computation section 33 makes "Yes" determination, it proceeds to S310. In the case where the digital computation section 33 makes a "No" determination, it repeatedly executes S300, thereby waiting until 290 μsec elapses.

Upon proceeding to S310 after making an "Yes" determination in S300, the digital computation section 33 instructs the detection signal generation section 42 to stop the output of the reverse-polarity signal Sb. Thus, the detection signal generation section 42 stops the output of the pulse signal to the electromotive force cell 24.

In S320 subsequent thereto, the Rpvs computation section 51 computes the internal resistance Rpvs of the electromotive force cell 24. Specifically, the Rpvs computation section 51 computes the internal resistance Rpvs of the electromotive force cell 24 by dividing a voltage change amount Vrpvs (=Vs1−Vs2), which is the difference between the sensor output signal Vs1 and the response signal Vs2, by the current value (1.22 mA) of the impedance detection signal Sa.

Since the processing of computing the internal resistance Rpvs is performed by the Rpvs computation section 51, the computed internal resistance Rpvs is reported from the Rpvs computation section 51 to the digital computation section 33.

In S330 subsequent thereto, the digital computation section 33 determines whether or not the timing to reset the switches (hereinafter referred to as the switch reset timing) has come about. In the case where the digital computation section 33 makes a "Yes" determination, it proceeds to S340. In the case where the digital computation section 33 makes a "No" determination, it repeatedly executes step 330, thereby waiting until the switch reset timing comes about.

Notably, the switch reset timing refers to the timing that comes first after execution of S310 among the timings at which the sampling period signal of the analog-to-digital conversion section 31 changes from the high level to the low level.

Upon proceeding to S340 after making a "Yes" determination in S330, the digital computation section 33 switches the state of the first switch 71 from the OFF state to the ON state, and switches the state of the second switch 73 from the ON state to the OFF state.

In S350 subsequent thereto, the digital computation section 33 determines whether or not 600 μsec has elapsed since start of the time measurement using the third timer. In the case where the digital computation section 33 makes a "Yes" determination, it proceeds to S360. In the case where the digital computation section 33 makes a "No" determination, it repeatedly executes S350, thereby waiting until 600 μsec elapses.

Upon proceeding to S360 after making a "Yes" determination in S350, the digital computation section 33 starts the pump current control processing.

In S370 subsequent thereto, the digital computation section 33 determines whether or not 1.0 msec has elapsed since start of the time measurement using the third timer. In the case where the digital computation section 33 makes a "Yes" determination, it proceeds to S380. In the case where the digital computation section 33 makes a "No" determination, it repeatedly executes S370, thereby waiting until 1.0 msec elapses.

Upon proceeding to S380 after making a "Yes" determination in S370, the digital computation section 33 starts the Ip output update processing.

In S390 subsequent thereto, the digital computation section 33 resets the second and third timers, to thereby stop the corresponding time measurements.

Upon completion of the processing in S390, the digital computation section 33 returns to S130.

After this, the digital computation section 33 repeatedly executes S130 to S390.

Namely, in the sensor control processing, the frequency band for the signals input to the analog-to-digital conversion section 31 is changed by switching the states of the first switch 71 and the second switch 73.

[1-3. Operation of Gas Detection System 1]

Figure 5:
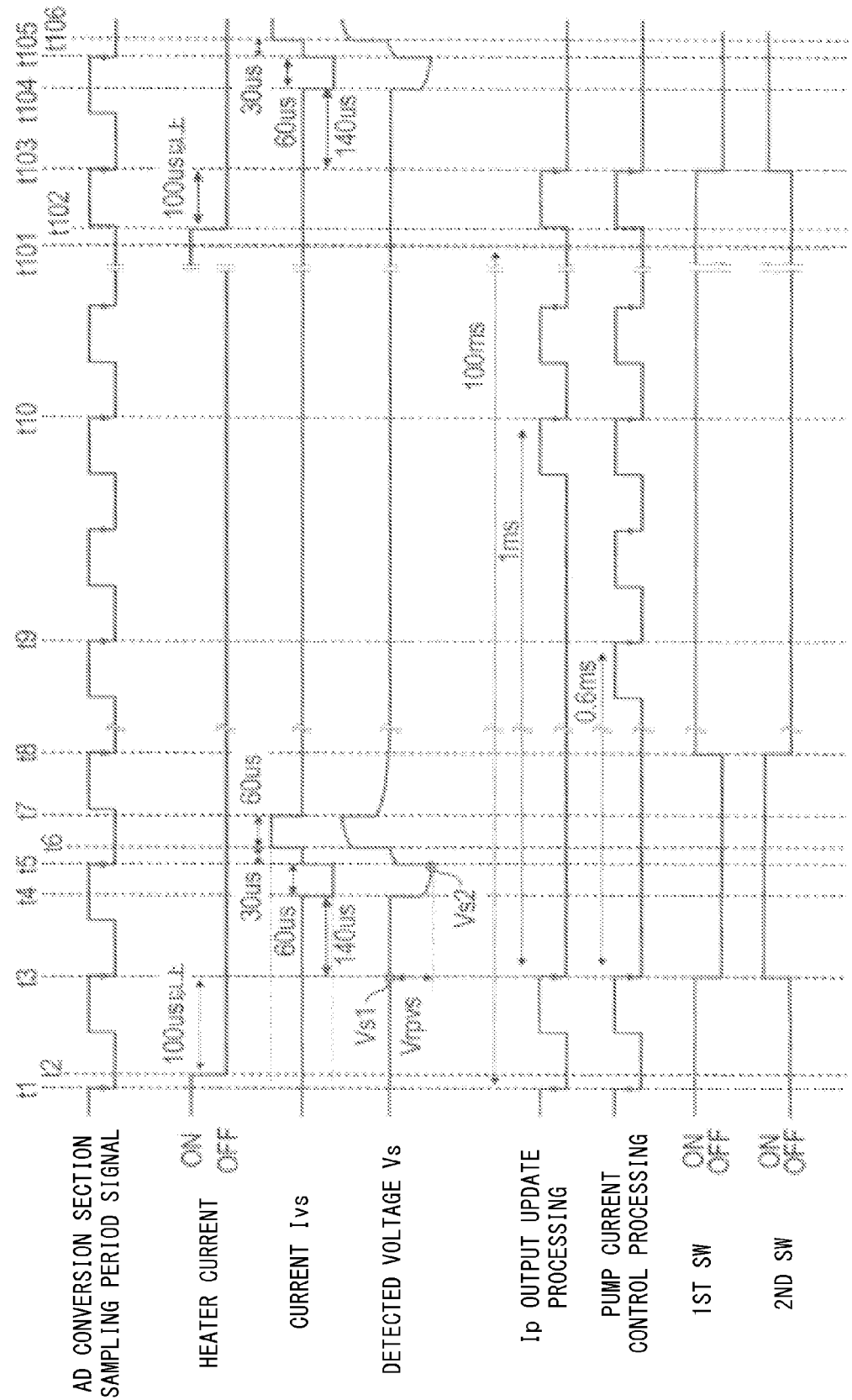
FIG. 5 is a timing chart showing the operation timings of relevant portions of the gas detection system.

FIG. 5 is a timing chart showing the operation timings of relevant portions of the gas detection system 1.

FIG. 5 shows the waveform of the sampling period signal of the AD conversion section 31, the waveform of a heater current applied to the heater 26, the waveform of a current Ivs flowing through the electromotive force cell 24, the waveform of the detection voltage Vs of the electromotive force cell 24, timings at which the output is updated by the Ip output update processing, timings at which the pump current Ip is updated by the pump current control processing, the state of the first switch 71, and the state of the second switch 73.

In FIG. 5, time t1 is a timing at which the time measurement performed by the first timer is restarted, and corresponds to the execution timing of S140 of the sensor control processing routine.

Time t2 is a timing at which the state of energization of the heater 26 is changed from the ON state to the OFF state, and corresponds to a timing at which a "Yes" determination is made in S150 of the sensor control processing routine.

Time t3 is a timing at which the pump current control processing is stopped; a timing at which the Ip output update processing is stopped; a timing at which the state of the first switch 71 is switched from the ON state to the OFF state; a timing at which the second switch 73 is switched from the OFF state to the ON state; and a timing at which the sensor output signal Vs1 is detected.

Time t3 corresponds to execution timings of S190, S200 and S210 of the sensor control processing routine. Strictly speaking, the execution timings of S190, S200 and S210 differ from each other. However, in the timing chart of FIG. 5, S190, S200 and S210 are executed at very close timings which can be assumed to be identical with one another.

Time t4 is a timing at which the detection signal generation section 42 starts inputting the impedance detection signal Sa to the electromotive force cell 24, and corresponds to the execution timing of S240 of the sensor control processing routine.

Time t5 is a timing at which the response signal Vs2 is obtained. Also, time t5 is a timing at which the detection signal generation section 42 stops the input of the impedance detection signal Sa to the electromotive force cell 24, and corresponds to execution timings of S260 and S270 of the sensor control processing routine. Strictly speaking, the execution timings of S260 and S270 differ from each other. However, in the timing chart of FIG. 5, S260 and S270 are executed at very close timings which can be assumed to be identical with each other.

Time t6 is a timing at which the detection signal generation section 42 starts inputting the reverse-polarity signal Sb to the electromotive force cell 24, and corresponds to the execution timing of S290 of the sensor control processing routine.

Time t7 is a timing at which the input of the reverse-polarity signal Sb from the detection signal generation section 42 to the electromotive force cell 24 is stopped, and corresponds to the execution timing of S310 of the sensor control processing routine.

Time t8 is a timing at which the state of the first switch 71 is changed from the OFF state to the ON state and the state of the second switch 73 is changed from the ON state to the OFF state, and corresponds to the execution timing of S340 of the sensor control processing routine.

Time t9 is a timing at which the pump current control processing is started, and corresponds to the execution timing of S360 of the sensor control processing routine.

Time t10 is a timing at which the Ip output update processing is started, and corresponds to the execution timing of S380 of the sensor control processing routine.

Time t101 is a point in time at which 100 msec has elapsed from the time t1. Also, time t101 is a timing at which the time measurement performed by the first timer is restarted just like at time t1, and corresponds to the execution timing of S140 of the sensor control processing routine.

Time t102 is a timing at which the state of energization of the heater 26 is changed (from the ON state to the OFF state) just like at the time t2, and corresponds to the timing at which a "Yes" determination is made in S150 of the sensor control processing routine.

Times t103, t104, t105 and t106 are timings corresponding to t3, t4, t5 and t6.

As mentioned above, in the gas detection system 1, by means of performing the above-described sensor control processing, the sensor control apparatus 2 brings the first switch 71 and the second switch 73 of the multiplexer 50 into different states between the case where the sensor output signal Vs1 which changes with a change in oxygen concentration in the measurement chamber is to be detected and the case where the response signal Vs2 which changes with a change in internal resistance Rpvs of the electromotive force cell 24 is to be detected.

Namely, in the case where the sensor output signal Vs1 which changes with a change in oxygen concentration in the measurement chamber is detected in order to perform the pump current control processing (i.e., the processing of feedback control of the pump current Ip supplied to the pump cell 14), the sensor control apparatus 2 changes the states of the first switch 71 and the second switch 73 such that the first switch 71 is set to the ON state and the second switch 73 is set to the OFF state. Meanwhile, in the case where the response signal Vs2 is detected in order to compute the internal resistance Rpvs of the electromotive force cell 24 (in other words, the temperature of the electromotive force cell 24), the sensor control apparatus 2 switches the states of the first switch 71 and the second switch 73 such that the first switch 71 is set to the OFF state and the second switch 73 is set to the ON state.

By changing the states of the first switch 71 and the second switch 73 as described above, the sensor control apparatus 2 changes the time constant of the low-pass filter section (composed of the low-pass filters 46 and 48) provided between the electromotive force cell 24 and the analog-to-digital conversion section 31, and changes the frequency band of the signal input from the electromotive force cell 24 to the analog-to-digital conversion section 31.

The first low-pass filter 46 and the second low-pass filter 48 are configured such that the time constant of the first low-pass filter 46 is greater than that of the second low-pass filter 48.

Thus, in the case where the sensor output signal Vs1 (detection voltage Vs) is detected in order to perform the pump current control processing, a signal that has passed through the first low-pass filter 46 is input to the analog-to-digital conversion section 31. Therefore, a signal whose frequency band is the same as that of the detection voltage Vs which changes with a change in oxygen concentration in the measurement chamber is input to the analog-to-digital conversion section 31.

Meanwhile, in the case where the response signal Vs2 is detected in order to compute the internal resistance Rpvs of the electromotive force cell 24, a signal that has passed through the second low-pass filter 48 is input to the analog-to-digital conversion section 31. Therefore, a signal whose frequency band is the same as that of the response signal Vs2 which changes with a change in internal resistance of the electromotive force cell 24 is input to the analog-to-digital conversion section 31.

[1-4. Effects]

As described above, in the gas detection system 1 of the present embodiment, since the sensor control apparatus 2 includes the first low-pass filter 46, the second low-pass filter 48 and the multiplexer 50, it is possible to switch the time constant between a value suitable for detection of the sensor output signal Vs1 and a value suitable for detection of the response signal Vs2.

Namely, the gas detection system 1 of the present embodiment has two low-pass filters having different time constants rather than a single low-pass filter having a fixed time constant, and changes the signal-passable frequency band by selectively using one of the two low-pass filters. Thus, it becomes possible to selectively input to the AD conversion section 31 the signal whose frequency band is the same as that of the sensor output signal Vs1 and the signal whose frequency band is the same as that of the response signal Vs2.

Since the time constant of the first low-pass filter 46 is set to be greater than the time constant of the second low-pass filter 48, the detection accuracy of the sensor output signal Vs1 and the detection accuracy of the response signal Vs2 can be improved.

Namely, in the case where the sensor output signal Vs1 is detected, a signal whose frequency band is the same as that of the sensor output signal Vs is input to the analog-to-digital conversion section 31 through the first low-pass filter 46, whereby the detection accuracy of the sensor output signal Vs1 is improved. In the case where the response signal Vs2 is detected, a signal whose frequency band is the same as that of the response signal Vs2 is input to the analog-to-digital conversion section 31 through the second low-pass filter 48, whereby the detection accuracy of the response signal Vs2 is improved.

According to the gas detection system 1 and the sensor control apparatus 2 of the present embodiment, a decrease in the detection accuracy of the sensor output signal Vs1 and the detection accuracy of the response signal Vs2 can be suppressed even in the case where the sensor control apparatus is configured to read these signals for use therein.

In addition, in the present embodiment, the timing at which the detection signal generation section 42 outputs the impedance detection signal Sa (S240) is set to come after a wait time (100 μsec) has elapsed (a "Yes" determination is made in S170) after switching the energization current supplied to the heater 26.

Namely, immediately after switching the current supplied to the heater 26, noise is generated due to the switching. However, when the wait time has elapsed, the level of the noise is satisfactorily lowered, whereby the influence of the noise on detection of the response signal Vs2 is mitigated.

As described above, according to the gas detection system 1 and the sensor control apparatus 2 of the present embodiment, a decrease in the detection accuracy of the response signal Vs2 can be suppressed.

[1-5. Correspondence Between Terms Appearing in the Description of the Present Embodiment and Terms Defining the Invention]

Here, the correspondence between terms appearing in the description of the present embodiment and terms defining the invention will be described.

The pump cell 14 corresponds to an example of the "second cell," the pair of porous electrodes 16 corresponds to an example of the "pair of electrodes," the electromotive force cell 24 corresponds to an example of the "first cell," the pair of porous electrodes 28 corresponds to an example of the "pair of electrodes," the first low-pass filter 46, the second low-pass filter 48 and the multiplexer 50 correspond to an example of the "time-constant variable filter section," the multiplexer 50 corresponds to an example of the "filter switching section," and the DAC control signal S1 corresponds to an example of the "control signal" of the invention.

2. Second Embodiment

As a second embodiment, a second gas detection system 101 will be described including a second sensor control apparatus 102 which includes a variable low-pass filter 81 in place of the "first low-pass filter 46, the second low-pass filter 48 and the multiplexer 50" of the first embodiment.

In the following description, the components of the second embodiment, which are the same as those of the first embodiment, are identified by the same symbols as those used to identify the corresponding components of the first embodiment. The second embodiment will be described by focusing on differences from the first embodiment.

Figure 6:
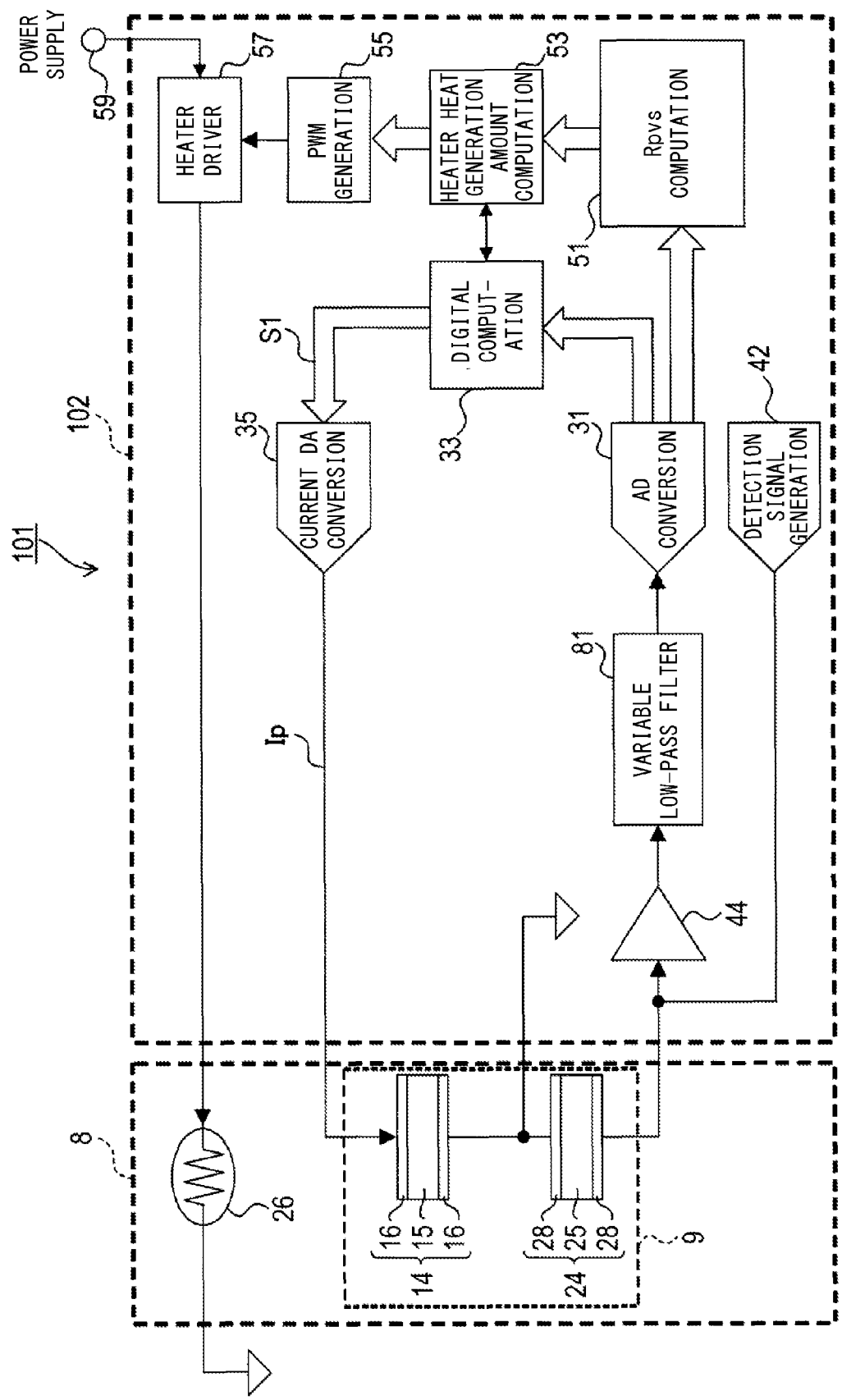
FIG. 6 is a block diagram showing the overall configuration of a second gas detection system.

FIG. 6 is a block diagram showing the overall configuration of the second gas detection system 101 of the second embodiment.

The second sensor control apparatus 102 of the second embodiment includes the variable low-pass filter 81 in place of the "first low-pass filter 46, the second low-pass filter 48 and the multiplexer 50" which are included in the sensor control apparatus 2 of the first embodiment.

Figure 7:
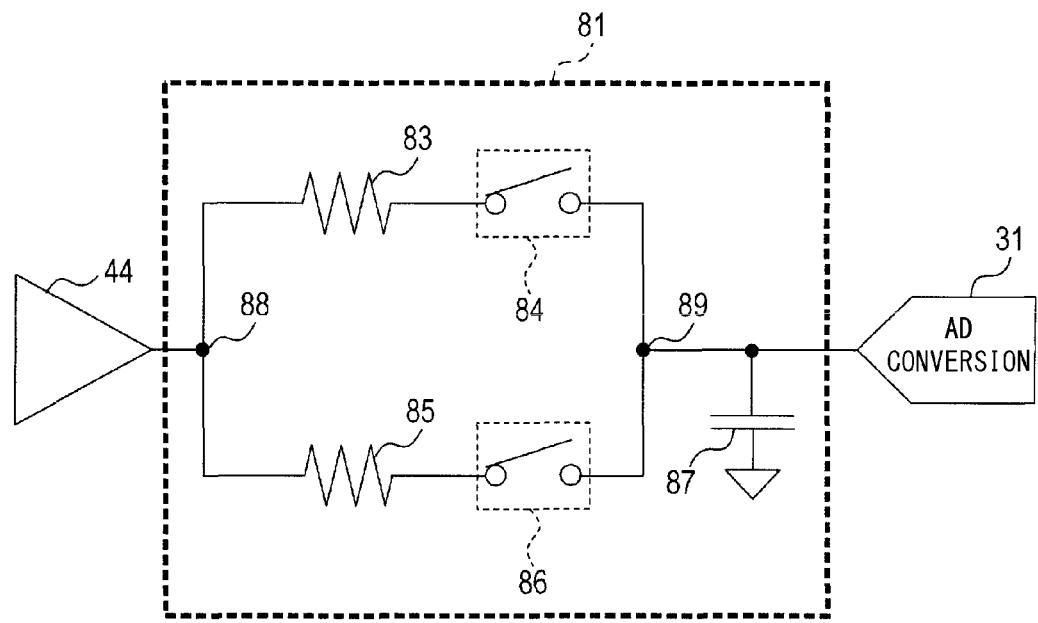
FIG. 7 is an explanatory diagram showing the internal configuration of a variable low-pass filter.

FIG. 7 is an explanatory diagram showing the internal configuration of the variable low-pass filter 81.

The variable low-pass filter 81 includes a third resistor element 83 having a resistance of 50 kΩ, a third switch 84, a fourth resistor element 85 having a resistance of 0.270 kΩ, a fourth switch 86 and a second capacitor element 87 having a capacitance of 22 nF.

In the variable low-pass filter 81, a series circuit including the third resistor element 83 and the third switch 84 and a series circuit including the fourth resistor element 85 and the fourth switch 86 are connected in parallel, a connection point 88 at which the third resistor element 83 and the fourth resistor element 85 are connected together is connected to the buffer 44, and a connection point 89 at which the third switch 84 and the fourth switch 86 are connected together is connected to the AD conversion section 31.

The second capacitor element 87 is connected between the ground line and the connection point 89 at which the third switch 84 and the fourth switch 86 are connected together.

The variable low-pass filter 81 forms a low-pass filter including the third resistor element 83 and the second capacitor element 87 when the third switch 84 is set to the ON state and the fourth switch 86 is set to the OFF state. In this case, the time constant of the variable low-pass filter 81 is the same as that of the first low-pass filter 46 of the first embodiment, and the variable low-pass filter 81 serves as a filter which extracts the sensor output signal Vs1 which changes with a change in oxygen concentration in the measurement chamber from those signals which change with a change in inter-terminal voltage of the electromotive force cell 24.

The variable low-pass filter 81 also forms a low-pass filter including the fourth resistor element 85 and the second capacitor element 87 when the third switch 84 is set to the OFF state and the fourth switch 86 is set to the ON state. In this case, the time constant of the variable low-pass filter 81 is the same as that of the second low-pass filter 48 of the first embodiment, and the variable low-pass filter 81 serves as a filter which extracts the response signal Vs2 which changes with a change in internal resistance of the electromotive force cell 24 from those signals which change with a change in inter-terminal voltage of the electromotive force cell 24.

Namely, the variable low-pass filter 81 is configured such that its time constant can be changed by changing the connection states of the third resistor element 83, the fourth resistor element 85 and the second capacitor element 87 by using the third switch 84 and the fourth switch 86.

In the sensor control processing of the second embodiment, the frequency band of the signal to be input to the analog-to-digital conversion section 31 is switched by controlling the states of the third switch 84 and the fourth switch 86 instead of the states of the first switch 71 and the second switch 73 of the first embodiment.

Thus, in the case where the sensor output signal Vs1 is detected in order to perform the pump current control processing, a signal that has passed through a low-pass filter including the third resistor element 83 and the second capacitor element 87 is input to the analog-to-digital conversion section 31. Namely, a signal whose frequency band is the same as that of the sensor output signal Vs1 which changes with a change in oxygen concentration in the measurement chamber is input to the analog-to-digital conversion section 31.

Meanwhile, in the case where the response signal Vs2 is detected in order to compute the internal resistance Rpvs of the electromotive force cell 24, a signal that has passed through a low-pass filter including the fourth resistor element 85 and the second capacitor element 87 is input to the analog-to-digital conversion section 31. Namely, a signal whose frequency band is the same as that of the response signal Vs2 which changes with a change in internal resistance of the electromotive force cell 24 is input to the analog-to-digital conversion section 31.

As described above, in the second gas detection system 101 of the second embodiment, the second sensor control apparatus 102 includes the variable low-pass filter 81, thereby making it possible to switch the time constant between a value suitable for detection of the sensor output signal Vs1 and a value suitable for detection of the response signal Vs2.

In addition, in the case where the sensor output signal Vs1 is detected, since a signal whose frequency band is the same as that of the sensor output signal Vs1 is input to the analog-to-digital conversion section 31 through the low-pass filter including the third resistor element 83 and the second capacitor element 87, the detection accuracy of the sensor output signal Vs1 is improved. In the case where the response signal Vs2 is detected, since a signal whose frequency band is the same as that of the response signal Vs2 is input to the analog-to-digital conversion section 31 through the low-pass filter including the fourth resistor element 85 and the second capacitor element 87, the detection accuracy of the response signal Vs2 is improved.

According to the second gas detection system 101 and the second sensor control apparatus 102 of the second embodiment, a decrease in the detection accuracy of the sensor output signal Vs1 and the detection accuracy of the response signal Vs2 can be suppressed even when the sensor control apparatus is configured to read these signals for use therein, just like in the first embodiment.

Here, the correspondence between terms appearing in the description of the present embodiment and terms defining the invention will be described.

The variable low-pass filter 81 corresponds to an example of the "time-constant variable filter section," and the third switch 84 and the fourth switch 86 correspond to an example of the "connection state changeover section."

3. Other Embodiments

Embodiments of the present invention have been described above. However, the present invention is not limited to the above-described embodiments, and may be implemented in various forms without departing from the spirit and scope of the claims appended hereto.

For example, in the above-described second embodiment, the variable low-pass filter 81 includes two resistor elements, two switches and a single capacitor element. However, a variable low-pass filter including two resistor elements, a single switch and a single capacitor element may be employed.

Figure 8:
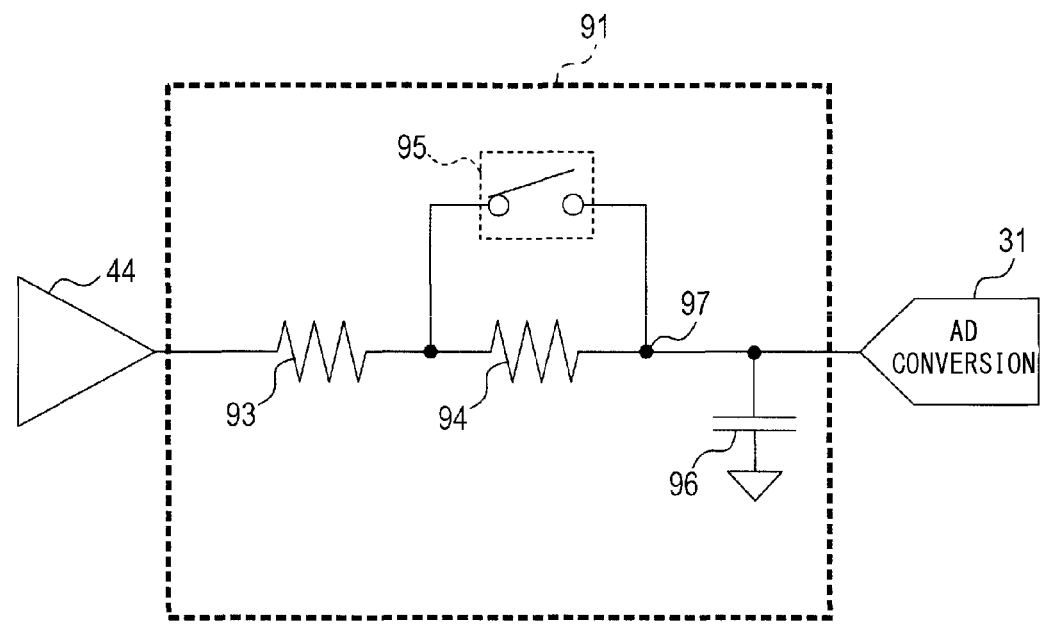
FIG. 8 is an explanatory diagram showing the internal configuration of a second variable low-pass filter.

FIG. 8 is an explanatory diagram showing the internal configuration of a second variable low-pass filter 91.

The second variable low-pass filter 91 includes a fifth resistor element 93 having a resistance of 0.270 kΩ, a sixth resistor element 94 having a resistance of 50 kΩ, a fifth switch 95, and a third capacitor element 96 having a capacitance of 22 nF.

In the second variable low-pass filter 91, the fifth resistor element 93 and the sixth resistor element 94 are connected in series, the sixth resistor element 94 and the fifth switch 95 are connected in parallel, an end of the fifth resistor element 93 is connected to the buffer 44, and an end of the sixth resistor element 94 is connected to AD conversion section 31.

The third capacitor element 96 is connected between the ground line and a connection point 97 at which the sixth resistor element 94 and the AD conversion section 31 are connected together.

When the fifth switch 95 is set to the OFF state, the second variable low-pass filter 91 forms a low-pass filter which includes a series circuit composed of the fifth resistor element 93 and the sixth resistor element 94, and a third capacitor element 96. In this case, the time constant of the second variable low-pass filter 91 is close to that of the first low-pass filter 46 of the first embodiment, and the second variable low-pass filter 91 serves as a filter which extracts the sensor output signal Vs1 which changes with a change in oxygen concentration in the measurement chamber from those signals which change with a change in inter-terminal voltage of the electromotive force cell 24.

In addition, when the fifth switch 95 is set to the ON state, the second low-pass filter 91 forms a low-pass filter including the fifth resistor element 93 and the third capacitor element 96. In this case, the time constant of the second variable low-pass filter 91 is the same as that of the second low-pass filter 48 of the first embodiment, and the second variable low-pass filter 91 serves as a filter which extracts the response signal Vs2 which changes with a change in internal resistance of the electromotive force cell 24 from those signals which change with a change in inter-terminal voltage of the electromotive force cell 24.

Namely, the second variable low-pass filter 91 is configured such that its time constant can be changed by changing the connection states of the fifth resistor element 93, the sixth resistor element 94 and the third capacitor element 96 by using the fifth switch 95.

In a sensor control apparatus including the second variable low-pass filter 91, the frequency band of the signal to be input to the analog-to-digital conversion section 31 is switched by controlling the state of the fifth switch 95 instead of the second switch 73 of the first embodiment.

Thus, in the case where the sensor output signal Vs1 is detected in order to perform the pump current control processing, a signal that has passed through the low-pass filter which includes the third capacitor element 96 and the series circuit composed of the fifth resistor element 93 and the sixth resistor element 94 is input to the analog-to-digital conversion section 31. Namely, a signal whose frequency band is the same as that of the sensor output signal Vs1 which changes with a change in oxygen concentration in the measurement chamber is input to the analog-to-digital conversion section 31, whereby the detection accuracy of the sensor output signal Vs1 is improved.

Meanwhile, in the case where the response signal Vs2 is detected in order to compute the internal resistance Rpvs of the electromotive force cell 24, a signal that has passed through the low-pass filter including the fifth resistor element 93 and the third capacitor element 96 is input to the analog-to-digital conversion section 31. Namely, a signal whose frequency band is the same as that of the response signal Vs2 which changes with a change in internal resistance of the electromotive force cell 24 is input to the analog-to-digital conversion section 31, whereby the detection accuracy of the response signal Vs2 is improved.

In the gas detection system configured as mentioned above, the sensor control apparatus includes the second variable low-pass filter 91. Therefore, the detection accuracy of the sensor output signal Vs1 and the detection accuracy of the response signal Vs2 can be improved by switching the time constant of the low-pass filter between a value suitable for detecting the sensor output signal Vs1 and a value suitable for detecting the response signal Vs2.

As described above, the gas detection system and the sensor control apparatus which include the second variable low-pass filter 91 can suppress a decrease in the detection accuracy of the sensor output signal response Vs1 and that of the response signal Vs2, even when the sensor control apparatus is configured to read these signals for use therein, just like in the second embodiment.

Here, the correspondence relation between terms appearing in the description of the present embodiment and terms defining the invention will be described.

The second variable low-pass filter 91 corresponds to an example of the "time-constant variable filter section," and the fifth switch 95 corresponds to an example of the "connection state changeover section" of the invention.

The resistances of the resistor elements of the above-described embodiments and the capacitances of the capacitor elements of the above-described embodiments are not limited to the above-described values, and may be set to appropriate values in accordance with the type of object gas and the purpose of gas detection.

The wait times and the times used for determining the sensor control processing of the above-described embodiments are not limited to the above-mentioned values, and may be set to appropriate values in accordance with the type of object gas and the purpose of gas detection.

In the above-described embodiments, the sensor control apparatuses are configured to execute the processing of computing the internal resistance Rpvs of the electromotive force cell 24 and the pump current control processing in parallel. However, the present invention is not limited to such a configuration. For example, the present invention may be applied to a sensor control apparatus configured such that the processing of computing the internal resistance Rpvs of the electromotive force cell 24 is periodically performed using the sensor output signal Vs1 and the response signal Vs2 obtained from the electromotive force cell, without performing the pump current control processing.

This application is based on Japanese Patent Application No. 2013-066736 filed Mar. 27, 2013, incorporated herein by reference in its entirety.

What is claimed is:

1. A sensor control apparatus for controlling a gas sensor including a sensor element which outputs a sensor output signal, the sensor output signal changing with a change in the concentration of a gas and which includes a first cell composed of a solid electrolyte body and a pair of electrodes, the sensor control apparatus comprising:
a detection signal generation section which generates an impedance detection signal for detecting the impedance of the first cell;
an analog-to-digital conversion section which receives the sensor output signal, the sensor output signal changing with a change in the concentration of the gas, or which receives a response signal generated by the first cell in response to the impedance detection signal, and which converts the analog value of the sensor output signal or the response signal to a digital value, the sensor output signal and the response signal being output from the first cell; and
a time-constant variable filter section which is a low-pass filter provided in a signal path between the first cell and the analog-to-digital conversion section and having a variable time constant,
the time-constant variable filter section having a time constant which changes such that the time constant at the time when the sensor output signal is input to the analog-to-digital conversion section is greater than the time constant at the time when the response signal is input to the analog-to-digital conversion section.

2. The sensor control apparatus as claimed in claim 1, wherein
the gas sensor includes a heater which brings the first cell into an activated state by supplying an energization current to the heater, and
the impedance detection signal is generated by the detection signal generation section after a predetermined wait time has elapsed after a time at which the energization current has been switched on.

3. The sensor control apparatus as claimed in claim 1, wherein the time-constant variable filter section includes:
a first low-pass filter which is used when the sensor output signal is input to the analog-to-digital conversion section;
a second low-pass filter which has a time constant smaller than that of the first low-pass filter and which is used when the response signal is input to the analog-to-digital conversion section; and
a filter switching section which connects the first low-pass filter between the first cell and the analog-to-digital conversion section when the sensor output signal is input to the analog-to-digital conversion section and which connects the second low-pass filter between the first cell and the analog-to-digital conversion section when the response signal is input to the analog-to-digital conversion section.

4. The sensor control apparatus as claimed in claim 1, wherein the time-constant variable filter section includes:
a single capacitor element;
a plurality of resistor elements; and
a connection state changeover section which forms a low-pass filter composed of the capacitor element and at least one of the resistor elements by connecting the capacitor element and the at least one resistor element,
the connection state changeover section changing the time constant of the low-pass filter by changing the state of connection between the capacitor element and the at least one resistor element.

5. The sensor control apparatus as claimed in claim 1, wherein
the sensor element further includes a second cell composed of a solid electrolyte body and a pair of electrodes; and
the sensor control apparatus comprises a digital computation section which computes, through digital computation, a control signal for controlling energization of the second cell, on the basis of the sensor output signal whose analog value is converted to a digital value by the analog-to-digital conversion section.

6. A gas detection system comprising:
a gas sensor including a sensor element which outputs a sensor output signal, said sensor output signal changing with a change in the concentration of a gas and which includes a first cell composed of a solid electrolyte body and a pair of electrodes; and
a sensor control apparatus for controlling the gas sensor as claimed in claim 1.

* * * * *